United States Patent [19]
Ho

[11] Patent Number: 5,457,246
[45] Date of Patent: Oct. 10, 1995

[54] PROCESS AND ARRANGEMENT FOR RECOVERY OF POLYOL PRODUCTION WASTES

[76] Inventor: Climent Ho, 3 Fl., No. 5, Lane 232, Sec. 3, Mu-Hsin Road, Taipei, Taiwan

[21] Appl. No.: 295,454

[22] Filed: Aug. 24, 1994

[51] Int. Cl.$^6$ .................... C07C 27/26; C07C 29/74
[52] U.S. Cl. .................... 568/854; 568/749; 568/844
[58] Field of Search .................... 568/844, 854, 568/749

[56] References Cited

U.S. PATENT DOCUMENTS

| | | | |
|---|---|---|---|
| 2,930,818 | 3/1960 | Wust | 568/854 |
| 4,105,575 | 8/1978 | Eckler | 568/854 |
| 4,277,620 | 7/1981 | Gupton et al. | 568/854 |
| 5,262,573 | 11/1993 | Smith | 568/854 |

*Primary Examiner*—Werren B. Lone
*Attorney, Agent, or Firm*—Davis Hoxie Faithfull & Hapgood

[57] ABSTRACT

A process and arrangement for separating and recovering polyol production wastes, including polyol, potassium or sodium phosphate and magnesium silicates, is disclosed. According to the invention, the polyol product waste and caustic salt are combined in a vessel, emulsified and then deemulsified. This causes the contents of the vessel to stratify into three layers. A first stream containing primarily magnesium silicates and a minor amount of caustic salt solution is withdrawn from the vessel and then water-washed. The water-washed magnesium silicates are then dehydrated and desiccated to obtain commercial grade magnesium silicates. The minor amount of caustic salt solution is dehydrated, crystallized and then desiccated to yield commercial grade anhydrous potassium or sodium phosphate. A second stream containing predominantly polyol oil is withdrawn from the vessel and subsequently filtered and dehydrated to obtain commercial grade polyol. The aforementioned process steps can be accomplished by an arrangement of commercially available equipment.

20 Claims, 3 Drawing Sheets

5,457,246

PROCESS AND ARRANGEMENT FOR RECOVERY OF POLYOL PRODUCTION WASTES

FIELD OF THE INVENTION

This invention relates to a process and an arrangement for the recovery of wastes from polyol production processes.

BACKGROUND OF THE INVENTION

One method for forming polyol involves polymerizing glycol in the presence of a potassium or sodium hydroxide catalyst. Wastes from polyol production via glycol polymerization include polyol, potassium or sodium phosphate and magnesium silicates. Such wastes are considered to be hazardous industrial wastes by the Environmental Protection Agency. Disposing of polyol production wastes is a problem; neither landfilling nor conventional incineration is acceptable. Further, to the extent such waste is disposed of rather than recovered, it represents the loss of potentially valuable products.

There is a need, therefore, for a method to process polyol production wastes which recovers polyol, potassium or sodium phosphate and magnesium silicates as commercially saleable products.

SUMMARY OF THE INVENTION

The aforementioned problems are solved by a novel process and arrangement for separating and recovering polyol production wastes using commercially available processing equipment.

The process according to the present invention comprises first combining the waste, along with excess potassium or sodium phosphate (caustic salt) solution, in an emulsification/de-emulsification reactor to effect a phase separation.

A first stream containing magnesium silicates and some polyol oil and caustic salt solution is withdrawn from the emulsification/de-emulsification reactor and then water-washed. The water-washed magnesium silicate, along with the caustic salt solution, is fed to a centrifugal dehydrator to remove moisture from the magnesium silicate. Solid magnesium silicate is withdrawn and then desiccated, resulting in commercial grade magnesium silicate.

Caustic salt solution is withdrawn from the centrifugal dehydrator and then vacuum dehydrated to remove moisture. Potassium or sodium phosphate is crystallized via two-stage crystallization and then desiccated to yield anhydrous potassium or sodium phosphate. A portion of the caustic salt solution drawn off the centrifugal dehydrator may be recycled to the emulsion reactor.

A second stream containing polyol oil and some magnesium silicate is withdrawn from the emulsification/de-emulsification reactor and subsequently filtered and dehydrated to yield a commercial grade polyol.

The water that is liberated as the caustic salt solution is dehydrated may be recovered and used as water wash make-up thereby minimizing waste products from the present invention. Further, the risk of combustion and/or explosion is reduced since water, rather than an organic solvent, is used to facilitate separation of the various components of the polyol production waste. Since substantially all of the components from the polyol waste are recovered into commercially saleable products, the process according to the present invention generates substantially no waste products.

The arrangement according to the present invention is a combination of commercially available equipment, as mentioned above, to accomplish the aforementioned process steps.

BRIEF DESCRIPTION OF THE DRAWINGS

Further features of the invention will become more apparent from the following detailed description of specific embodiments thereof when read in conjunction with the accompanying drawing wherein.

DETAILED DESCRIPTION OF THE INVENTION

Figure 1:
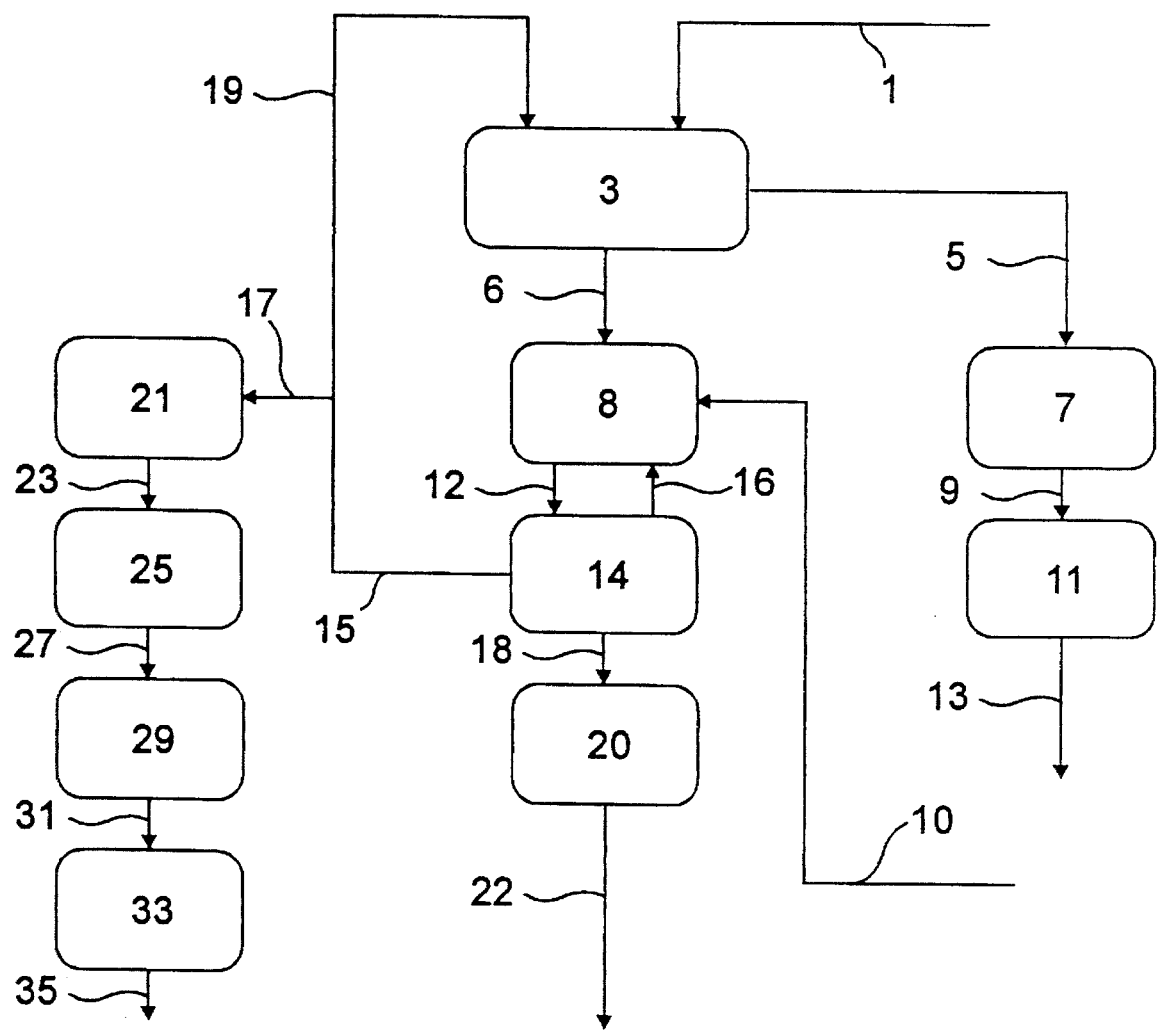
FIG. 1 shows a flow diagram of the process and arrangement according to the present invention.

FIG. 1 is a block flow diagram of a process and an arrangement according to the present invention. The feed 1, which is a mixture of polyol, potassium or sodium phosphate (caustic salt) and silicates, is charged to an emulsification/de-emulsification reactor 3 for separation of these components. The feed is in the form of a filter cake. The filter cake is a damp-sticky-slurry-like material which is most easily fed manually to the reactor. Alternatively, suitable materials handling devices may be used for delivering the feed 1 to the emulsification/de-emulsification reactor.

The polyol will typically have a molecular weight ranging from about 100 to 8000 and a hydroxide number ranging from about 24 to 500. The silicates are typically magnesium silicates.

The feed 1 is mixed with additional caustic salt solution. The additional caustic solution should be about 0.5 to 2 times the weight of the feed 1. The salt concentration of the caustic solution should be such that salt does not drop out of solution in the emulsification reactor 3. A 30 weight percent solution has been found to give satisfactory results. The reactor 3 charge may also include a caustic salt solution recycle stream 19, which is recycled from downstream processing.

The emulsification/de-emulsification reactor 3, like all equipment used in the arrangement according to the invention, is a conventional, commercially available vessel, well known to those skilled in the art. The emulsification/de-emulsification reactor 3 should have means for agitating the reactor contents, such as a variable-speed motor connected to a shaft having blades or paddles, and a means for temperature control such as a steamheating system.

The emulsification/de-emulsification reactor 3 is operated so that the mixture stratifies into three layers or phases. The top layer is composed of polyol, typically containing about 2 to 10 weight percent of water. The middle layer is an aqueous caustic salt solution, typically containing about 1 to 5 weight percent of polyol. The bottom layer is primarily composed of magnesium silicates, typically containing about 1 to 10 weight percent polyol.

To stratify the waste components as described above, the emulsification/de-emulsification reactor 3 should first be operated at low temperature and agitated at high speed to emulsify feed and caustic salt solution. An agitation rate of about 400 rpm for about 30 minutes has been found to be suitable to emulsify the mixture. Temperature should be maintained between about 120° to 205° F. (49° to 96° C.). In a preferred embodiment, the temperature is initially set at about 120° F. and heat is applied during agitation to a maximum reactor temperature of about 205° F. During this step, it is important to avoid boiling the contents of the reactor.

The emulsification/de-emulsification reactor 3 is next operated at lower agitation speeds and higher temperatures to de-emulsify the reactor contents. The temperature should be raised to at least 210° F. (99° C.), and preferably raised to the boiling point of the mixture. Boiling should occur at about 220° F. (104° C.), which varies with the specific composition of the mixture being processed. An agitation rate of about 200 rpm for about 90 minutes has been found to be suitable to de-emulsify the mixture.

Finally, the agitation rate is further reduced and the temperature is decreased to about 200° to 205° F. After about 30 minutes at low agitation and 200° to 205° F., the reactor contents should stratify into three layers as described above. An agitation rate of about 50 rpm has been found to be suitable for this step.

After stratification, the upper-most layer comprising polyol and the lower-most layer comprising magnesium silicates are removed from the emulsification/de-emulsification reactor 3 for further processing. At least two outlets are provided for this purpose. The polyol phase outlet is preferably located on the side of the emulsification/de-emulsification reactor 3 at an appropriate location as a function of the operating liquid level in the reactor 3. A slurry outlet for the magnesium silicates is typically located at the bottom of the reactor 3.

A slurry stream 6 of magnesium silicate solids, some caustic salt solution, and a minor quantity of polyol is fed to a counter-current water wash 8. Make-up water is supplied to the water wash 8 via stream 10. A minimal amount of make-up water is required as moisture recovered in downstream processing of the caustic salt solution can be recycled to the water wash 8. A stream 12 containing water-washed magnesium silicate solids and the caustic salt solution is removed from the water wash 8 and charged to a centrifugal dehydrator 14 where the moisture content of the magnesium silicate solids is reduced and the caustic salt solution and polyol is separated from the magnesium silicate solids. A recycle 16 of dehydrated magnesium silicate to the water wash 8 is established. This may be a manual operation. A dehydrated magnesium silicate product 18, now free of potassium/sodium phosphate contaminants, is fed to a desiccator 20 for final moisture removal. Desiccation yields commercial grade magnesium silicates 22. Typically, the moisture content of the desiccated product 22 is below 0.3% and the organic impurities are less than 0.5%.

Substantially all of the caustic salt solution that was removed from the emulsification/de-emulsification reactor 3 is withdrawn via stream 15 from the centrifugal dehydrator 14. A portion of the flow of stream 15 may be recycled to the emulsification/de-emulsification reactor 3 as the caustic salt solution recycle 19. The balance of stream 15, identified in FIG. 1 as stream 17, is dehydrated in vacuum dehydrator 21. A concentrated caustic salt solution 23 from the vacuum dehydrator 21 is then subjected to two-stage crystallization. In the first stage, concentrated solution 23 is fed to a crude crystallization tank 25. The crude crystalline product 27 is charged to a recrystallizer 29 to yield a finely crystallized potassium/sodium phosphate product 31 having a particle size smaller than 1 millimeter. The finely crystallized product 31 is desiccated in desiccator 33 to yield commercial grade anhydrous potassium/sodium phosphate powder 35.

Where a recycle is employed, stream 17 contains substantially all the potassium or sodium phosphate that enters the process from the filter cake feed 1. Thus, a balance is maintained between the caustic entering and leaving the system. If the present invention is operated without the caustic salt solution recycle 19, substantially all the caustic withdrawn with the magnesium silicates will be recovered as the anhydrous powder 35. Since more caustic may be removed than enters in the filter cake feed 1, additional caustic make-up may be required to maintain the desired amount of excess caustic solution when operating without a caustic recycle 19.

Figure 2:
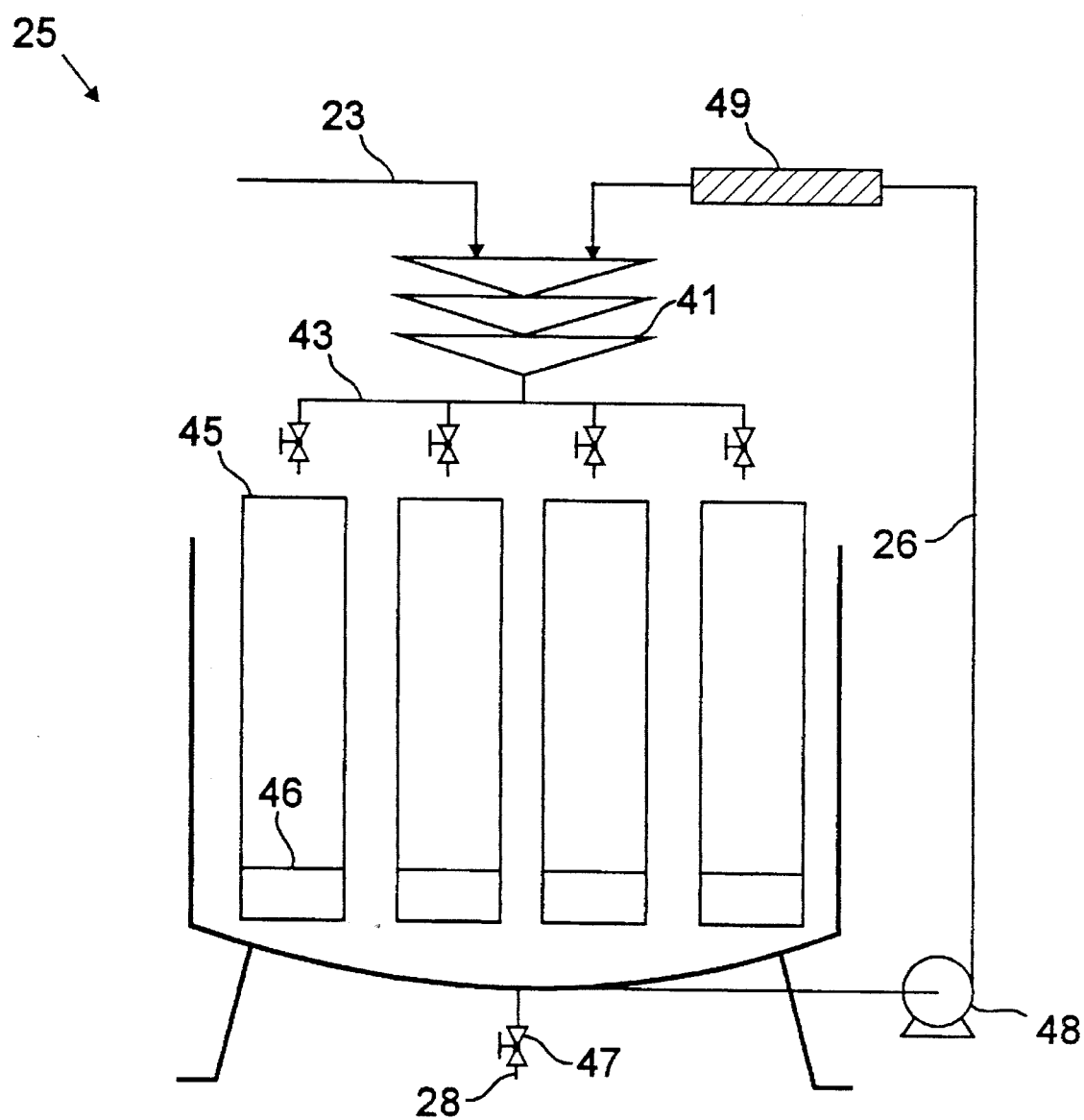
FIG. 2 shows an embodiment of a crude crystallizer suitable for use in the present invention.

As previously noted, the caustic salt solution typically contains 1 to 5 weight percent polyol. This polyol will contaminate the caustic salt product if not removed. As shown in FIG. 2, a polyol-absorbing material 41, such as a polypropylene fiber cloth, should contact the caustic solution in both the crude crystallization tank 25 and the recrystallizer 29 to remove the polyol. As the moisture content of the solution decreases, polyol will be absorbed by the fiber cloth.

Figure 3:
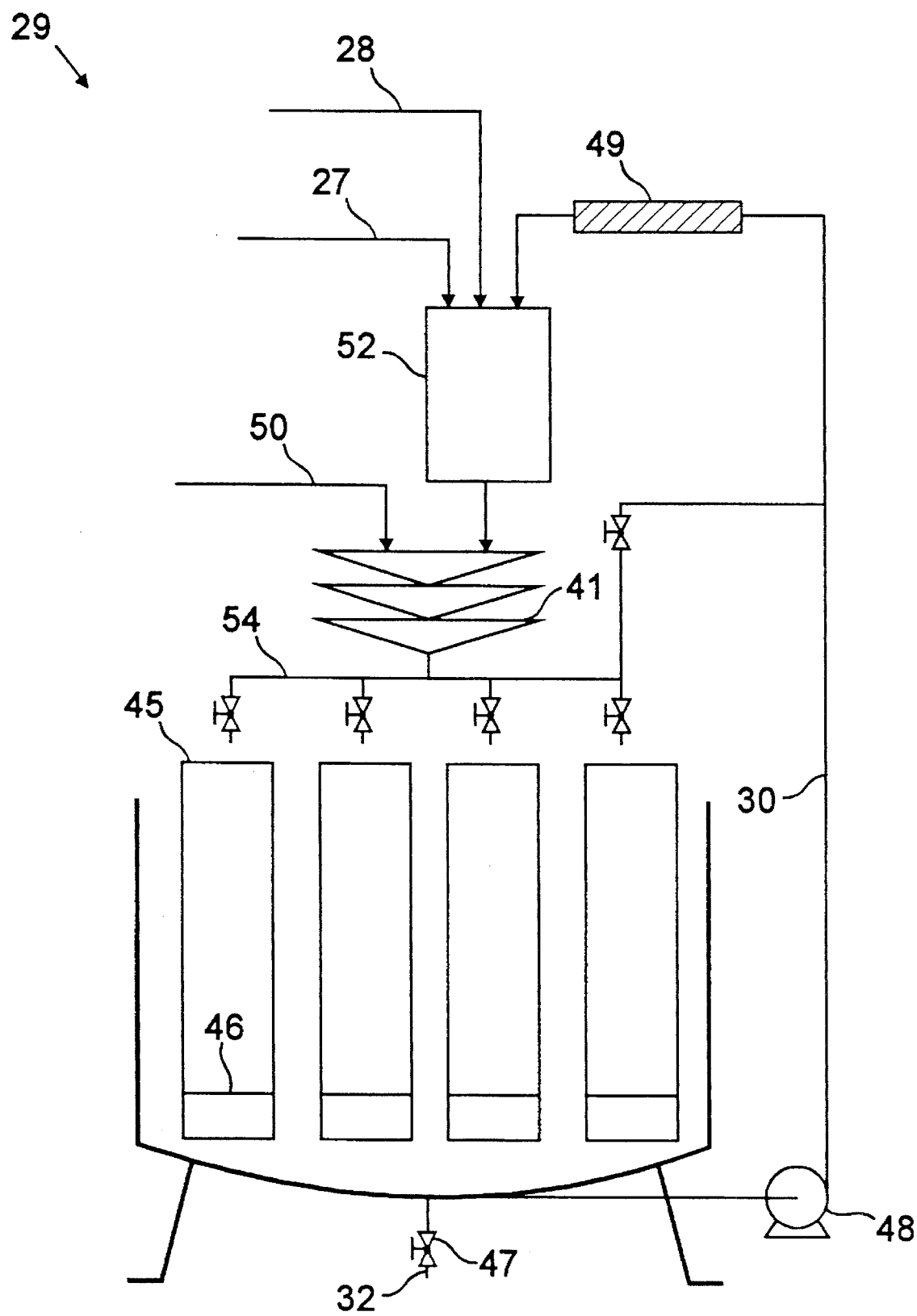
FIG. 3 shows an embodiment of a recrystallizer suitable for use in the present invention.

The crystallizers, which may be static-tank crystallizers or other suitable crystallizers known to those skilled in the art, should be modified to prevent the crystallized material from contacting the polyol which is removed. One way to modify the crystallizers is shown in FIGS. 2 and 3, wherein inner tanks and a crystallizer-feed distributor are provided. The crystallizers should be operated in a multi-pass manner for optimum recovery. This may be accomplished by recycling the caustic solution.

FIG. 2 shows an embodiment of the crude crystallizer 25. Concentrated caustic salt solution 23 charged to the crude crystallizer contacts a polyol-absorbing material 41 and is then distributed to the inner tanks 45 via the crude crystallizer-feed distributor 43. A screen 46 is located near the bottom of each inner tank 45. The screen 46 functions as a sieve to retain the material that crystallizes. The screen should be selected to retain material having a particle size greater than about 1 millimeter. The inner tanks 45 are bottomless so that the caustic solution flows out the bottom of the inner tanks. Effluent caustic solution 28 is drained from the crude crystallizer 25 at valve 47. Some of the caustic drained from the crude crystallizer is recycled via recycle pump 48. Recycled caustic 26 is heated by a heating device 49 before it is reintroduced into the crude crystallizer.

FIG. 3 shows an embodiment of the recrystallizer 29. Crude crystalline product 27, effluent caustic solution 28 from the crude crystallizer 25 and recycled caustic 30 are mixed in the crystalline dissolving tank 52. The mixture, as well as fresh water 50, contacts the polyol absorbing material 41 and is then distributed to the inner tanks 45 via the recrystallizer feed distributor 54. The lower portion of each inner tank 45 contains a screen 46 as in the crude crystallizer. As will be appreciated by those skilled in the art, this screen should be sized to retain crystallized material suitable for commercial sale after dessication. Effluent caustic solution 32 is drained from the recrystallizer 29 at valve 47. Some of the effluent caustic is recycled via recycle pump 48. Some recycled caustic 30 is heated by a heating device 49 before re-introduction into the recrystallizer. It should be understood that other modifications for preventing polyol contact with crystallized material will occur to those skilled in the art, which modifications are within the contemplated scope of the present invention.

Stream 5, containing predominately polyol with some moisture, caustic salt and other solid impurities, is removed from the emulsification/de-emulsification reactor 3 and fed to a filtration unit 7 to remove solid impurities including caustic salt. The filtrate 9 flows to a dehydrator 11, such as a vacuum dehydrator, where moisture is removed to yield a commercial grade polyol product 13. The vacuum dehydrator should be operated at about 100 torr and 212° F. The moisture content of the product 13 should be less than about 0.2 percent and the potassium and sodium content below 50 ppm.

Thus, magnesium silicates and polyol are removed from the emulsification/de-emulsification reactor 3, leaving caustic solution. The caustic solution remaining in the reactor is substantially all the additional caustic which was mixed with the feed 1 prior to emulsification/de-emulsification. The caustic solution is suitable for re-use with additional feed 1 as long as the salt concentration is such that the salt remains in solution. If the salt concentration is too high, the caustic solution should be drained from the emulsification/de-emulsification reactor 3 and processed like stream 17 to recover potassium or sodium phosphate powder.

Polyol production wastes were treated by a process and arrangement according to the present invention. The results are shown in Table 1 below.

TABLE 1

Treatment of Polyol Production Wastes

|  | Sample 1 | Sample 2 | Sample 3 | Sample 4 |
| --- | --- | --- | --- | --- |
| Polyol |  |  |  |  |
| Molecular Wt. | 400 | 1000 | 4800 | 7000 |
| Hydroxyl No. | 280 | 112 | 35 | 24 |
| Stream Comp., Wt % |  |  |  |  |
| Polyol | 45 | 40 | 49 | 51 |
| Potassium Phosphate | 13 | 14 | 12 | 12 |
| Magnesium Silicates | 42 | 46 | 39 | 37 |
| Excess $KH_2PO_3$ (30% sol.) | 1.25 | 1.50 | 1.50 | 1.80 |
| Excess to Feed Conversion Temp. (°F.) | 205 | 210 | 214 | 215 |
| Polyol Recovery, wt % | 97.4 | 98.1 | 97.7 | 99.0 |

The caustic salt recovered from samples 1–4 using the process according to the invention was 99.8 percent pure.

It should be understood that the embodiments described herein are illustrative of the principles of this invention and that modifications may be implemented by those skilled in the art without departing from the scope and spirit of the invention.

I claim:

1. A method for treating polyol production waste containing polyol, caustic salt and magnesium silicates comprising the steps of:
   (a) forming a mixture of the polyol production waste and a caustic salt solution in a vessel physically adapted to agitate and heat the mixture, wherein the weight ratio of the caustic salt solution to the polyol production waste is in the range of about 0.5:1.0 to 2.0:1.0;
   (b) causing the mixture to stratify into a first, second and third phase, by agitating the mixture at temperature ranging from about 120° to 210° F. the first phase comprising polyol, the second phase comprising caustic salt solution and the third phase comprising magnesium silicates;
   (c) removing the third phase comprising magnesium silicates from the vessel, wherein a minor amount of the caustic salt solution is also removed;
   (d) water-washing the magnesium silicates and the minor amount of the caustic salt solution;
   (e) removing moisture from the magnesium silicates;
   (f) crystallizing at least some of the minor amount of the caustic salt solution; and
   (g) removing the first phase comprising polyol from the vessel.

2. The method of claim 1 wherein the caustic salt is selected from the group consisting of potassium phosphate and sodium phosphate.

3. The method of claim 2 wherein the caustic salt solution is comprised of the caustic salt.

4. The method of claim 2 wherein the step of causing the mixture to stratify comprises the steps of:
   (a) emulsification at about 120° F. to 205° F. and at a high rate of agitation;
   (b) de-emulsification at at least about 210° F. and a lower rate of agitation than in step (a); and
   (c) settling at about 200° F. to 205° F. and a lower rate of agitation than in step (b).

5. The method of claim 2 wherein the step of water-washing comprises contacting the magnesium silicates phase and the minor amount of the caustic salt solution phase with water flowing counter-current to the flow of the caustic salt solution phase and the magnesium silicates phase.

6. The method of claim 2 wherein the step of removing moisture from the magnesium silicates phase comprises using a centrifugal dehydrator and a desiccator.

7. The method of claim 2 wherein the step of crystallizing the caustic salt solution comprises:
   (a) forming a concentrated caustic salt solution by dehydrating the minor amount of the caustic salt solution;
   (b) forming a finely crystallized caustic salt by crystallizing the dehydrated concentrated salt solution of step (a); and
   (c) desiccating the finely crystallized caustic salt.

8. The method of claim 7 wherein the step of forming a concentrated caustic salt solution comprises using a vacuum dehydrator.

9. The method of claim 7 wherein the step of forming a finely crystallized caustic salt comprises using a two-stage crystallizer to produce a caustic salt having a particle size smaller than 1 millimeter.

10. The method of claim 1 wherein the step of removing the first phase comprises:
    (a) filtering the polyol; and
    (b) dehydrating the polyol.

11. The method of claim 2 wherein the step of dehydrating the polyol phase comprises using a vacuum dehydrator to lower the moisture content of the polyol phase to less than about 0.2 weight percent.

12. The method of claim 1 wherein a portion of the minor amount of the caustic salt solution phase is recycled to the vessel such that the weight of the minor amount of the caustic salt in the caustic salt solution phase that is not recycled is substantially equal in amount to the weight of the caustic salt contained in the polyol production waste.

13. The method of claim 6 wherein the step of removing moisture from the magnesium silicates phase comprises reducing moisture to less than about 0.3 percent.

14. The method of claim 10 wherein the step of dehydrating the polyol comprises reducing moisture to less than about 0.2 percent.

15. An arrangement for the recovery of polyol, caustic salt and magnesium silicates from polyol production waste comprising:
   (a) an emulsifier/de-emulsifier vessel for forming an emulsion of the polyol production waste and a caustic salt solution and for de-emulsifying into a first, second and third phase, the first phase comprising polyol, the second phase comprising caustic salt solution and the third phase comprising magnesium silicates;
   (b) a filter for filtering the first phase;
   (c) a vacuum dehydrator for dehydrating the first phase;
   (d) a water-wash vessel for removing impurities from the third phase;
   (e) a centrifugal dehydrator for dehydrating the third phase;
   (f) a desiccator for removing substantially all moisture from the third phase;
   (g) a vacuum dehydrator for dehydrating caustic salt solution;
   (h) a two-stage crystallizer for forming a finely crystallized caustic salt; and
   (i) a desiccator for removing substantially all moisture from the finely crystallized caustic salt.

16. The arrangement of claim 15 wherein the two-stage crystallizer comprises a crude crystallization tank and a recrystallizer.

17. The arrangement of claim 15 wherein the two-stage crystallizer includes a polyol-absorbing material.

18. The arrangement of claim 17 wherein the polyol-absorbing material is a polypropylene fiber cloth.

19. The arrangement of claim 17 wherein the two-stage crystallizer comprises means for preventing crystallized material from contacting polyol removed in the two-stage crystallizer.

20. The arrangement of claim 17 wherein the two-stage crystallizer comprises bottomless inner tanks having screens for retaining crystallized material.

* * * * *